(12) United States Patent
Janchitraponvej

(10) Patent No.: US 6,540,989 B2
(45) Date of Patent: *Apr. 1, 2003

(54) SELF-WARMING RINSE OUT HAIR CARE COMPOSITIONS

(75) Inventor: Ben Janchitraponvej, Niles, IL (US)

(73) Assignee: Unilever Home & Personal Care USA, division of Conopco, Inc., Chicago, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/437,884

(22) Filed: Nov. 9, 1999

(65) Prior Publication Data

US 2001/0016201 A1 Aug. 23, 2001

Related U.S. Application Data

(60) Provisional application No. 60/146,995, filed on Aug. 3, 1999.

(51) Int. Cl.$^7$ ................................................. A61K 7/06
(52) U.S. Cl. ................ 424/70.1; 424/70.28; 424/70.22; 424/70.12
(58) Field of Search ............................ 424/70.1, 70.12, 424/70.28, 70.22

(56) References Cited

U.S. PATENT DOCUMENTS

| | | | |
|---|---|---|---|
| 4,902,499 A | | 2/1990 | Bolish, Jr. et al. |
| 4,976,956 A | * | 12/1990 | Noe .......................... 424/70 |
| 5,328,685 A | | 7/1994 | Janchitraponvej et al. |
| 5,332,569 A | | 7/1994 | Wood et al. |
| 5,393,521 A | * | 2/1995 | Lance-Gomez et al. . 424/70.12 |
| 5,656,280 A | | 8/1997 | Herb et al. |
| 5,876,705 A | * | 3/1999 | Uchiyama et al. ....... 424/70.12 |

FOREIGN PATENT DOCUMENTS

| | | |
|---|---|---|
| EP | 0027730 | 4/1981 |
| EP | 0617953 | 10/1994 |
| WO | 00/38621 | 7/2000 |

OTHER PUBLICATIONS

International Search Report Application No. PCT/EP/00/06991 mailed Dec. 18, 2000.

* cited by examiner

Primary Examiner—Thurman K. Page
Assistant Examiner—Amy E Pulliam
(74) Attorney, Agent, or Firm—Milton L. Honig

(57) ABSTRACT

An anhydrous or substantially anhydrous self-warming rinse-out composition which comprises:
   a) a glycol,
   b) a quaternary ammonium compound,
   c) an amidoamine, and
   d) a silicone.

9 Claims, No Drawings

SELF-WARMING RINSE OUT HAIR CARE COMPOSITIONS

This application claims the benefit of provisional application No. 60/146,995, filed Aug. 3, 1999.

BACKGROUND OF THE INVENTION

It would be desirable to provide anhydrous self-warming hair care compositions. These rinse-out compositions are first applied to the hair, and then when contacted with water they generate heat and give a perception of warmth, to the user. The perception of warmth is desirable, because it serves as a signal or cue to the user, that the composition works, and provides warmth and relation.

Alternately, water could be applied to hair first and then the rinse-out compositions could be applied, or water and rinse-out compositions could be simultaneously applied to the hair. All of these methods would generate heat.

Such, rinse-out compositions can take the form of shampoos, conditioners, or 2 in 1 products that is compositions that are; both shampoos and conditioners.

Known anhydrous self-warming rinse-out hair care compositions have deficiencies in rheology and conditioning ability. It would be desirable to overcome these deficiencies in rheology and conditioning ability.

Publication and products which relate to the field of the invention are as follows:

The Product: Lux Self-Warming Conditioner Treatment—1998

Product Label from the Andrew Jergens Company, for the Biore Facial Musk—copyright 1998. The Biore Self-Heating Mask is a facial mask which contains sodium silicoaluminate. On contact with water, this mask heats up.

U.S. Pat. No. 5,328,685—July, 1994 (incorporated by reference) describes a clear conditioning composition comprising an amidoamine salt, said amidoamine salt comprising an amidoamine compound of a specified formula that is neutralized with a suitable acid.

SUMMARY OF THE INVENTION

The invention relates to an anhydrous, self-warming rinse-out hair care composition which comprises:
  a) at least one glycol;
  b) at least one quaternary ammonium compound;
  c) at least one amidoamine; and
  d) at least one silicone.

Compositions of the invention can take the form of conditioners, shampoos, or 2 in 1 products.

The invention also relates to a method for deep conditioning the hair with self-warning and/or cleansing the hair with self-warming, which comprises contacting the hair with a composition of the invention and with water.

The invention also relates to a process for preparing a composition of the invention.

DETAILED DESCRIPTION OF THE INVENTION

As used herein % means weight % of the total composition unless otherwise specified. Degrees are in degrees Celsius unless otherwise specified. "Substantially anhydrous" means less than about 2 weight %, or more preferably less than about 1 weight % water. "Self-warming" means that when a composition of the invention is contacted with water, heat is evolved and the resulting composition may rise in temperature.

Compositions of the invention are anhydrous or substantially anhydrous rinse-off hair care compositions which, can take the form of conditioners, shampoos or 2 in 1 products.

Compositions of the invention comprise:
  a) at least one glycol;
  b) at least one quaternary ammonium compound;
  c) at least one amidoamine; and
  d) at least one silicone.

More specifically, compositions of the invention can comprise:
  a) from about 30% to about 95% glycol;
  b) from about 1% to about 10% quat;
  c) from about 0.05% to about 5% amidoamine; and
  d) from about 0.05% to about 5% silicone.

As noted above, the compositions of the invention are either anhydrous or substantially anhydrous. Also as noted about compositions of the invention generate heat upon coming into contact with water. This heat is called the heat of dissolution of glycol. Since this heat is to be generated when the composition is being used by the consumer, water must be kept from the compositions of the invention until used by the consumer. That is why the compositions of the invention are lighter anhydrous or substantially anhydrous.

What follows is a description of the ingredients used in the compositions of the invention.

Glycols

The following list of glycols which may be used in compositions of the invention is meant to be illustrative and not limiting. These glycols can be hydrophilic, glycols such as the following: propylene glycol, ethylene glycol, glycerin, butylene glycol and mixtures thereof.

The following list of polyethylene glycols which may used in compositions of the invention is meant to be illustrative and not limiting. These polyethylene glycols are as follows: PEG-4, -6, -8, -9, -10, -12, -14, -16, -18, -20, -200, -900, and -600. Also included are beheneth-5 and -10, PEG-7 betanophthol and PEG-15 butanediol. Also included are buteth-3 carboxylic acid, butoxynol-5 and -1; PEG-8, C12–C18 ester, C12–13 pareth-7 carboxylic acid; C11–C15 pareth-7 carboxylic acid, C12–C15 pareth-7 carboxylic acid.

The following list of polyethylene glycols which may be used in compositions of the invention is meant to be illustrative and not limiting. These polyethylene glycols are as follows: PEGs-4, -6, -8, -9, -10, -12, -14, -16, -18, -20, -200, -400 and -600. Also included are beheneth-5 and -10, peg-7 betanaphthol and PEG-15 butanediol. Also included are buteth-3 carboxylic acid, butoxynol-5 and -19, PEG-8 C12–18 ester, C12 13 pareth-7 carboxylic acid, Cl 1–15 pareth-7 carboxylic acid, Cl 2–15 pareth-7 carboxylic acid, C14–15 pareth-8 carboxylic acid, PEG-8 caprate, PEG-8 caprylate, PEG-8 caprate/caprylate, PEG-6, and -8 caprylic/capric glycerides, capryleth-6 and -9 carboxylic acids, ate, PEG-8 caprylate. Also included are ceteareth-2, -3, -4, -5, -5, -6, -7, -8, -10, -11, -12, -13, -15, -6, -17, -18, and -20; choleth-10 and -20; PEG-3 cocamide, PEG-5 cocamide, PEG-6 cocamide, PEG-7 cocamide, PEG-11 cocamide, PEG-20 cocamide; PEG-2 cocamine, PEG-3 cocamine, PEG-5 cocamine, PEG-10 cocamine, PEG-15 cocamine, and PEG-20 cocamine; PEG-5 cocoate, PEG-8 cocoate, PEG-15 cocoate; coceth-3, 5, and -8; PEG-2 dilaurate, PEG-4 dilaurate, PEG-6 dilaurate, PEG-8 dilaurate, PEG-12 dilaurate, PEG-20 dilaurate, PEG-4 dioleate, PEG6 dioleate, PEG-8 dioleate, PEG-10 dioleate, PEG-12 dioleate, and isosteareth-2, isosteareth-3, isosteareth-10, isosteareth-12, and isosteareth-20; isoceteth-10, and -20; isodeceth-4, -5, and -6; isostereath-2, -3, 10, -12, and -20; PEG-3 lauramine oxide; PEG-2 laurate, PEG-4 laurate, PEG-6 laurate, PEG-8 laurate, PEG-9 laurate, PEG-10 laurate, PEG-12 laurate, PEG-14 laurate, and PEG-20 laurate; laureth-1, -2, -3, -4, -5, -6, -7, -8, -9, -10, -11, -12, -13, -14, -15, -16,and -20; oleth-2, -3, -4, -5, -6, -7, -8, -9, -10, 12, -15, -16, and -20; stereath-2, -3, -4, -5, -6, -7, -10, -11, -13, -14, -15, -16, and -20; and trideceth-3, -5, -6, -9, -10, -11, -12, and -15.

Quaternary Ammonium Compounds

The following list of quaternary ammonium compounds which may be included in the compositions of the invention is intended to be illustrative and not limiting.

The following list of quaternary ammonium compounds which may be used in compositions of the invention is meant to be illustrative and not limiting. These compounds have the general structural formula: N[R 1 R2R3R4]+X-where R, is an alkyl group including from about 8 to about 18 carbon atoms, R2 is selected from the group consisting of an alkyl group including from about 8 to about 18 carbon atoms, a hydrogen atom, a methyl group, an ethyl group, a hydroxymethyl group and a hydroxyethyl group, R4 is selected from the group consisting of a hydrogen atom, a methyl group, an ethyl group, a hydroxymethyl group, and a hydroxyethyl group; and X is an anion. The quaternary nitrogen of the quaternary ammonium compound can also be a component of a heterocyclic moiety such as morpholine or pyridine. The anion can be an anion such as chloride, methosulfate, ethosulfate, nitrate, bromide, tosylate, acetate or phosphate.

The quaternary ammonium compounds have one or two long chain alkyl groups having from about 8 to about 18 carbon atoms, the long chain alkyl groups can also include in addition to, or in replacement of carbon and hydrogen atoms, ether linkages or similar water solubilizing linkages the remaining two or three substituents of the quaternary nitrogen can be hydrogen or benzyl; or short chain alkyl or hydoxyalkyl groups such as methyl ethylhydroxymethyl or hydroxyethyl groups, or combinations thereof either diether of the same or different identity Exemplary quaternary ammonium compounds include but are not limited to lauratrimonium chloride, quaternium-16, lauralkonium chloride, dicetyidimonium chloride, cetylpyridinium chloride, soyatrimonium chloride, mytrimonium chloride, cetrimonium chloride, PEG-2 cocomonium chloride, PEG-2 cocoyl quaternium-4, PEG 2 oleyl quarenium 4 polyquaternium-6,-7, -11, -5, -24, and mixtures thereof, these quaternary ammonium compounds are described in U.S. Pat. No. 5,656,280 which is hereby incorporated by reference. Other water dispersible ammonium compounds include distearyl dimonium chloride, and behenyl trimmonium chloride.

Amidoamines

The following list of amidoamines which may be used in compositions of the invention is meant to be illustrative and not limiting. These amide amines included those described in U.S. Pat. No. 5,328,685, which is hereby incorporated by reference.

Amidoamines, included but are not limited to diethylaminoethylstearamine, isosteamidopropyl dimethylamine, cocamide propyidimethylamine, ricinoleamido propyidimethylamine, oleamidopropyldimethylamine, behenamidopropyl dimethylamine, palmitamidopropyl dimethylamine, stearamido ethyidiethylamine, stearamidopropyldimethylamine, soy amidopropyl dimethylamine, and dimethylaminopropyl myristamide.

Silicones

The following list of silicones which may be used in compositions of the invention is meant to be illustrative and not limiting. These silicones are as follows: a polyalkyl siloxane, a polyaryl siloxane or a polyalkylaryl siloxane.

Mixtures of volatile silicones as cyclotetrasiloxane, cyclopentasiloxane, or cyclohexasiloxane are useful. Mixtures of the nonvolatile silicone compounds are also useful. The so-called "rigid silicones", as described in U.S. Pat. No. 4,902,499, herein incorporated by reference, having a viscosity above 600,000 cs at 20C and a weight average molecular weight of at least about 500,000, also are useful in compositions of the present invention. A phenyltrimethicone also is useful as a nonvolatile silicone compound. Also useful is a mixture of a low molecular weight silicone fluid and a higher molecular weight silicone gum. Silicones which are useful in compositions of the invention are described in U.S. Pat. No. 5,656,280.

Nonvolatile silicones include siloxane or siloxane mixtures having a viscosity of greater than 1 0 centistokes. Nonlimiting examples include dimethicone, dimethiconol, amodimethicones, phenyl trimethicone and silicone copolyols.

Any combination of silicones and amidoamines listed just above are preferred for use in compositions of the invention.

Conditioner materials in general, may be selected from the group consisting of quaternary ammonium compounds, amidoamines, silicones, cationic polymers, and hydrocarbons and fatty alcohol either alone or together with the proviso that there must be included in compositions of the invention at least one amidoamine in combination with at least one silicone. Without wishing to be bound by any theory, it is believed that the compositions of the invention, function as conditioners, for example, because the amidoamine acts as a deposition aid for the silicone. Again an important feature of the compositions of the invention is that it contain at least one amidoamine, and at least one silicone.

The following list of fatty alcohols which may be used in compositions of the invention is meant to be illustrative and not limiting. These fatty alcohols include a fatty alcohol or fatty acid, or derivative thereof, or a mixture of any of these having a chain length of from about 8 to about 36 carbon atoms. More preferably from about 12 to about 22 carbon atoms. These materials may be predominantly linear or may be branched. Preferred are stearyl alcohol, cetyl alcohol, behenyl alcohol, lauryl alcohol, myristyl alcohol, and coco alcohol.

Another important feature of the present invention is that its viscosity has a range between about 1,000 or 2,000 centistokes to about 30,000 centistokes, more preferably between about 5,000 centistokes to about 18,000 centistokes. This viscosity is achieved by using one or more of the quaternary ammonium compounds described above. Because the composition has the above described viscosities, its use with water, which activates the glycol dissolution system generates heat, and causes the consumer to have the perception of warmth.

Optional Ingredients

Optional ingredients which can be used in compositions of the invention are now described.

Nonionic surfactants suitable for use in compositions of the invention include condensation products of aliphatic C8–C18 primary or secondary linear or branched chain alcohols or phenols with alkylene oxides, usually ethylene oxide, and generally having from 6 to 30 ethylene oxide groups.

Other suitable nonionics include mono- or di-alkyl alkanolamides. Examples include coco mono- or diethanolamide and coco mono-isopropanolamide. Further suitable nonionic surfactants are the alkylpolyglycosides (APG's). Typically, the APG is one which comprises an alkyl group connected (optionally via a bridging group) to a block of one or more glycosyl groups.

Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms.

Examples include lauryl amine oxide, cocodimethyl suiphopropyl betaine and preferably lauryl betaine, cocamidopropyl betaine and sodium cocamphopropionate.

Further surfactants which may be suitable for use in conditioning shampoos in accordance with the invention include one or more anionic surfactants instead of or in addition to any of those surfactants mentioned above. Those surfactants must be dispersed or mixed in glycols, PEGS, etc.

Suitable anionic surfactants are the alkyl sulphates, alkyl either sulphates, alkaryl sulphonates, alkaroyl isethionates, alkyl succinate, alkyl sulphosuccinates, N-alkoyl sarcosinates, alkyl phosphates, alkyl ether phosphates, alkyl ether carboxylates, and alpho-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 1 0 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauroyl isethionate and sodium N-lauryl sarcosinate. The most preferred anionic surfactants are sodium lauryl sulphate, triethanolamine laurylسulphate, triethanolamine monolauryl phosphate, sodium lauryl ether sulphate 1 EO, 2EO and 3EO, ammonium lauryl sulphate and ammonium lauryl ether sulphate 1 EO, 2EO and 3EO.

As further optional components for inclusion in the compositions of the invention, the following may be mentioned: pH adjusting agents, viscosity modifiers, cosmetic fillers such as talc, kaolin; pearlescers, opacifiers, suspending agents, preservatives, coloring agents, dyes, proteins, herb and plant extracts, polyols and other moisturizing.

Compositions of the invention can be made by using processes which are known in the art or by using processes which are analogous to those known in the art. Compositions of the invention can be made by using starting materials which are known in the art or by using starting materials which are obtainable from materials that are known in the art.

Other surfactants include alkyl sulfates, alkyl ether sulfonates, alkyl sulfonates, fatty acids, and the like. Many additional anionic cleansing surfactants are described in McCutcheon's, DETERGENTS and EMULSIFIERS 1989 ANNUAL published by McCutcheon's Publishing Company.

Conditioner materials in general may be selected from the group consisting of quaternary ammonium compounds, amidoamines, silicones, cationic polymers, and hydrocarbons and fatty alcohol either alone or together with the proviso that there must be included in compositions of the invention at least one amidoamine in combination with at least one silicone. Without wishing to be bound by any theory, it is believed that the compositions of the invention, function as conditioners, for example, because the amidoamine acts as a deposition aid for the silicone. Again an important feature of the compositions of the invention is that it contains at least one amidoamine, and at least one silicone.

The following list of fatty alcohols which may be used in compositions of the invention is meant to be illustrative and not limiting. These fatty alcohols include a fatty alcohol or fatty acid, or derivative thereof, or a mixture of any of these having a chain length of from about 8 to about 36 carbon atoms. More preferably from about 12 to about 22 carbon atoms. These materials may be predominantly linear or may be branched. Preferred are stearyl alcohol, cetyl alcohol, behenyl alcohol, lauryl alcohol, myristyl alcohol, and coco alcohol.

Nonionic surfactants suitable for use in compositions of the invention include condensation products of aliphatic C8–C18 primary or secondary linear or branched chain alcohols or phenols with alkylene oxides, usually ethylene oxide, and generally having from 6 to 30 ethylene oxide groups.

Other suitable nonionics include mono- or di-alkyl alkanolamides. Examples include coco mono- or diethanolamide and coco mono-isopropanolamide. Further suitable nonionic surfactants are the alkylpolyglycosides (APG's). Typically, the APG is one which comprises an alkyl group connected (optionally via a bridging group) to a block of one or more glycosyl groups.

Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms.

Examples include lauryl amine oxide, cocodimethyl sulphopropyl betaine and preferably lauryl betaine, cocamidopropyl betaine and sodium cocamphopropionate.

Further surfactants which may be suitable for use in conditioning shampoos in accordance with the invention include one or more anionic surfactants instead of or in addition to any of those surfactants mentioned above. Those surfactants must be dispersed or mixed in glycols, PEGS, etc.

Suitable anionic surfactants are the alkyl sulphates, alkyl either sulphates, alkaryl sulphonates, alkaroyl isethionates, alkyl succinate, alkyl sulphosuccinates, N-alkoyl sarcosinates, alkyl phosphates, alkyl ether phosphates, alkyl ether carboxylates, and alpho-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 1 0 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauroyl isethionate and sodium N-lauryl sarcosinate. The most preferred anionic surfactants are sodium lauryl sulphate, triethanolamine lauryl sulphate, triethanolamine monolauryl phosphate, sodium lauryl ether sulphate 1 EO, 2EO and 3EO, ammonium lauryl sulphate and ammonium lauryl ether sulphate 1 EO, 2EO and 3EO.

As further optional components for inclusion in the compositions of the invention, the following may be mentioned: pH adjusting agents, viscosity modifiers, cosmetic fillers such as talc, kaolin; pearlescers, opacifiers, suspending agents, preservatives, coloring agents, dyes, proteins, herb and plant extracts, polyols and other moisturizing.

Compositions of the invention can be made by using processes which are known in the art or by using processes which are analogous to those known in the art. Compositions of the invention can be made by using starting materials which are known in the art or by using starting materials which are obtainable from materials that are known in the art.

Other surfactants include alkyl sulfates, alkyl ether sulfonates, alkyl sulfonates, fatty acids, and the like. Many additional anionic cleansing surfactants are described in McCutcheon's, Detergents and Emulsifiers, 1989 Annual published by McCutcheon's Publishing Company.

Compositions of the invention may be applied before or after the application of water. Compositions of the invention may be used simultaneously with water.

If the composition of the invention is a conditioner, it may be applied to the hair, usually with the fingers, and then rinsed out. If the composition of the invention is a shampoo or a 2 in 1 product, it may be applied to the hair with water, lathered, and then rinsed out.

Compositions of the invention which are conditioners are opaque conditioners, generally.

Compositions of the invention are made by mixing the glycol and heating to about 65° C. to about 70° C. for at least 30 minutes; cooling the batch to about 60° C., adding the silicone, cooling to about 45° C., adding more silicone, and fragrance, etc. and further cooling, to about room temperature.

The following examples are meant to be illustrative and not limiting.

Composition of the Invention

| Item # | Description | Actual Wt % |
|---|---|---|
| 1 | PEG 200 | 69.6190000 |
| 2 | CETYL/STEARYL ALCOHOL, 100% ACTIVE | 2.5000000 |
| 3 | BEHENTRIMONIUM CHLORIDE | 2.0000000 |
| 4 | DICETYLDIMONIUM CHLORIDE/PG, 68%/27 ACT | 1.0000000 |
| 5 | STEARAMIDOPROPYL DIMETHYLAMINE, 100% ACT | .5000000 |
| 6 | CITRIC ACID | .1000000 |
| 7 | STEARETH-2, 99% ACTIVE | 1.0000000 |
| 8 | STEARETH-21 | 1.0000000 |
| 9 | GLYCERIN, USP, 99.7% ACTIVE | 18.6000000 |
| 10 | DIMETHICONE 60,000 CS | 2.0000000 |
| 11 | CYCLOPENTASILOXANE, 99% ACTIVE | 1.0000000 |
| 12 | OTHER | 95 TO 100 |

Manufacturing Steps:

1. Into a manufacturing tank, add PEG 200 and beginning to heat to 70° C.;
2. Add items #5, stearamidopropyl dimethylamine and item #6, citric acid, mix at 30° C.;
3. Add items #2, cetyl stearyl alcohol, #3, behentrimonium chloride and #4, dicetyidimonium chloride;
4. Add items 7, steareth 2 and #8, steareth 21, mix until homogeneous;
5. Add pre-mix, items #9 & 10 at 60° C.;
6. At 40° C. add item #11;
7. Add item #12.

Original Lux Formula
Composition: (Control)

| Item # | Description | Actual Wt % |
|---|---|---|
| 1 | GLYCERIN, USP, 99.7% ACTIVE | 15.00 |
| 2 | DIMETHICONE 60,000 CS | 2.00 |
| 3 | GLYCERIN, USP, 99.7% ACTIVE | 3.60 |
| 4 | PEG 200 | 71.15 |
| 5 | CETYL/STEARYL ALCOHOL | 2.50 |
| 6 | BEHENTRIMONIUM CHLORIDE | 2.00 |
| 7 | STEARETH-2 99% ACTIVE | 1.00 |
| 8 | STEARETH-21 | 1.00 |
| 9 | DL-PANTHENOL, 99% ACTIVE | .10 |
| 10 | CYCLOPENTASILOXANE 99% ACTIVE | 1.00 |
| 11 | FRAGRANCE | .65 |

Manufacturing Steps:

1. In the Ross add Item #4, PEG 200, add Item #5, and add Item #7 Steareth-2 and Item #8 Steareth-21 and Item #9, DL-Panthenol.
2. Heat batch to 65–70° C. (149–158 F.) with anchor cowles and vacuum
3. Once the batch reaches 65–70° C. mix for 30 minutes
4. Cool to 60° F.
5. Glycerin premix to the batch. Use homomixer, anchor.
6. Cool to 45° C.
7. Item #10, Cyclopentasiloxane and Item #11, fragrance.

Composition: (Control)
Composition "B"

| Item # | Description | Actual Wt % |
|---|---|---|
| 1 | PEG 200 | 70.629 |
| 2 | DICETYLDIMONIUM CHLORIDE/PG, 68%/27% ACTIVE | 2.500 |
| 3 | CETYL/STEARYL ALCOHOL, 100% ACTIVE | 2.500 |
| 4 | STEARETH-2 99% | 1.000 |
| 5 | STEARETH-21 | 1.000 |
| 6 | DIMETHICONE 60,000 CS | 2.000 |
| 7 | CYCLOPENTASILOXANE, 99% ACTIVE | 1.000 |
| 8 | GLYCERIN, USP, 99.7% ACTIVE | 18.600 |
| 9 | OTHER | 95 TO 100 |

Manufacturing Steps:

1. In the Ross Item #1, PEG 200, begins to heat to 68–72° C.;
2. Add item #2, dicetyldimonium chloride;
3. Add item #3, Cetyl stearyl alcohol;
4. Add Steareth-2;
5. Add Steareth-21;
6. Mix the batch for 40 minutes or until homogeneous;
7. Cool to 60° C.;
8. Add pre-mix items #6 & 8. Use homomixer, anchor,
9. Cool to 45° C.;
10. Add item #7 cyclopentasilixane;
11. Add item #9.

| Composition "D" (Control) | | |
|---|---|---|
| Item # | Description | Actual Wt % |
| 1 | PEG 200 | 70.65 |
| 2 | CETYL/STEARYL ALCOHOL, 100% ACTIVE | 2.50 |
| 3 | BEHENTRIMONIUM CHLORIDE | 2.00 |
| 4 | DICETYLDIMONIUM CHLORIDE/PG, 68%/27% ACTIVE | .50 |
| 5 | STEARETH-2, 99% ACTIVE | 1.00 |
| 6 | STEARETH-21 | 1.00 |
| 7 | GLYLCERIN, USP, 99.7% ACTIVE | 18.60 |
| 8 | DL-PANTHENOL, 99% ACTIVE | 0.10 |
| 9 | DIMETHICONE 60,000 CS | 2.00 |
| 10 | CYCLOPENTASILOXANE, 99% ACTIVE | 1.00 |
| 11 | FRAGRANCE | .65 |

Manufacturing Steps:

1. In the Ross Item #1, PEG 200, heat to 65–70° C.;
2. Add item #2, Cetyl/Stearyl alcohol;
3. Add item #3, Behentrimonim Chloride;
4. Add item #4, Dicetyidimonium Chloride;
5. Add item #5, Steareth-2;
6. Add item #6, Steareth-21;
7. Mix the batch for 40 minutes or until homogeneous;
8. Cool to 60° C.;
9. Add pre-mix item #7 (Glycerin) & 9 (Dimethicone) cool to 45° C.;
10. Add remaining ingredients.

| Composition "C" (Control) | | |
|---|---|---|
| Item # | Description | Actual Wt % |
| 1 | PEG 200 | 68.1290000 |
| 2 | DICETYLDIMONIUM CHLORIDE/PG, 68%/27% ACTIVE | 2.5000000 |
| 3 | CETYL/STEARYL ALCOHOL, 100% ACTIVE | 5.0000000 |
| 4 | STEARETH-2, 99% ACTIVE | 1.0000000 |
| 5 | STEARETH-21 | 1.0000000 |
| 6 | DIMETHICONE 60,000 CS | 2.0000000 |
| 7 | CYCLOPENTASILOXANE, 99% ACTIVE | 1.0000000 |
| 8 | GLYCERIN, USP, 99.7% ACTIVE | 18.6000000 |
| 9 | OTHER | 95 TO 100 |

Manufacturing Steps:

1. In the Ross add item #1, PEG 200. Heat to 65–70° C.;
2. Add item #2, dicetyidimonium chloride;
3. Add item #3, cetyl/stearyl alcohol;
4. Add item #4, steareth-2;
5. Add item #5, steareth-21;
6. Mix for 40 minutes or until batch becomes homogeneous;
7. Cool to 60° C.;
8. Add pre-mix items #6 (dimethicone) & 8 (glycerin). Use homomixer, anchor;
9. Cool to 45° C. Add items #7 and #9.

Another composition of the invention is:

| Composition E (Composition of the Invention) | | |
|---|---|---|
| Item # | Description | Actual Wt % |
| 1 | PEG 200 | 65.2496 |
| 2 | STEARAMIDOPROPYL DIMETHYLAMINE | 3.0 |
| 3 | CITRIC ACID | 0.50 |
| 4 | DICETYLDIMONIUM CHLORIDE/PG | 1.0 |
| 5 | BEHENYL ALCOHOL | 2.5 |
| 6 | BEHENTRIMONIUM CHLORIDE | 2.0 |
| 7 | SILICA | 1.5 |
| 8 | GLYCERIN | 18.6 |
| 9 | DIMETHICONE 60,000 CS | 2.0 |
| 10 | STEARYL ALCOHOL AND CETEARETH-20 | 3.0 |
| 11 | SILK POWDER | 0.0001 |
| 12 | SODIUM PCA | 0.0002 |
| 13 | DL PANTHENOL | 0.0001 |
| 14 | FRAGRANCE | 0.65 |

Manufacturing Steps:

1. Into a manufacturing tank, add PEG 200 and beginning to heat to 70° C.;
2. Add Stearamidopropyl Dimethylamine and Citric acid. Mix for 20 minutes;
3. Add Dicetyidimonium Chloride;
4. Add Behenyl Alcohol;
5. Add Behentrimonium Chloride;
6. Add Silica;
7. Add pre-mix Glycerine & Silicone. Mix the batch for half hour;
8. Add Stearyl Alcohol and Ceteareth-20;
9. Mix the batch for half hour and beginning to cool to 30° C.;
10. Add the remaining ingredients;
11. Pass through homogenizer;

pH 6.6 TO 7.7.

Viscosity ranges from 7,000 to about 14,000 cps.

TABLE 1

| Composition | odification of Lux Self Warming Conditioner Formula | A | B | C | D | Commercial Conditioner Extra Body | Commercial Conditioner Extra Moisturizer |
|---|---|---|---|---|---|---|---|
| PEG 200 | 71.15 | 69.619 | 70.629 | 68.129 | 70.65 | 0 | 0 |
| Behenyl Alcohol | 0 | 0 | 0 | 0 | 0 | 0 | 0 |
| Behentriumonium Chloride | 2 | 2 | 0 | 0 | 2 | 0 | 0 |
| Dicetyldimonium Chloride | 0 | 1 | 2.5 | 2.5 | .5 | 2.1 | 0 |
| Stearamidopropyl | 0 | .5 | 0 | 0 | 0 | .5 | .5 |

TABLE 1-continued

| Composition | odification of Lux Self Warming Conditioner Formula | A | B | C | D | Commercial Conditioner Extra Body | Commercial Conditioner Extra Moisturizer |
|---|---|---|---|---|---|---|---|
| Dimethylamine | | | | | | | |
| Citric Acid | 0 | .1 | 0 | 0 | 0 | .09 | 0 |
| Dimethicone | 2 | 2 | 2 | 2 | 2 | .1 | 0 |
| Cyclomethicone | 1 | 1 | 1 | 1 | 1 | 1.8 | 1.6 |
| Cetyl/ Stearyl Alcohol | 2.5 | 2.5 | 2.5 | 5 | 2.5 | 3.25 | 4.72 |
| Glycerin | 18.6 | 18.6 | 18.6 | 18.6 | 18.6 | 0 | .05 |
| Stearyl Octyldimonium Methosulfate | 0 | 0 | 0 | 0 | 0 | 0 | 1.75 |

Composition A is a composition of the invention.

Wet combing tests were done by Instron devices, which is a method known in the art. Composition A of the invention was similar in wet combing properties to the Commercial Conditioner Extra Moisturizer.

Composition A was superior in wet combing properties to all of the other compositions in Table 1.

TABLE 2

| Formula Number | Combing Force (Instron) Maximum Load | Temperature Increase |
|---|---|---|
| Mod. Lux Self-Warming Conditioner | 14.39 | 7 C |
| A | 10.57 | 8 C |
| B | 12.68 | 8 C |
| C | 13.41 | 8 C |
| D | 12.56 | 8 C |
| E | 10.34 | 8 C |
| Commercial Extra Moisturizer Conditioner (Bench Mark) | 10.34 | 0 |
| Commercial Extra Body Conditioner (Bench Mark) | 12.77 | 0 |

Wet combing tests were done by Instron device, which is a method known in the art. Compositions A and E of the invention were similar in wet combing properties to the Commercial Conditioner Extra Moisturizer. Compositions A and E were superior in wet combing properties to all of the other compositions in Table 2.

What is claimed is:

1. An anhydrous or substantially anhydrous self-warming rinse-out composition in the form of a shampoo which comprises:
   a) from about 30% to about 95% glycol,
   b) from about 1% to about 10% quaternary ammonium compound,
   c) from about 0.05% to about 5% amidoamine,
   d) from about 0.5% to about 5% silicone, and
   e) an anionic surfactant.

2. A composition in accordance with claim 1 wherein the glycol is PEG-200.

3. A composition in accordance with claim 1 wherein the quaternary ammonium compound is Behentrimonium Chloride.

4. A composition in accordance with claim 1 wherein the amidoamine is Stearamidopropyl Dimethylamine.

5. A composition in accordance with claim 1 wherein the silicone is Dimethicone (60,000 cs).

6. A composition in accordance with claim 1 wherein the amidoamine is Stearamidopropylamine and the silicone is Dimethicone 60,000 cs.

7. A composition according to claim 1 which further comprises a pH adjusting agent, a viscosity modifier a preservative, a coloring agent and a moisturizing agent.

8. A method for treating hair which comprises contacting said hair
   (i) with water and then
   (ii) a composition according to claim 1; or
   (i) with a composition according to claim 1 and then
   (ii) water;
   or
   (i) with a composition according to claim 1 and water simultaneously.

9. A method for cleansing hair which comprises contacting said hair with a shampoo composition according to claim 1 and water.

* * * * *